United States Patent [19]

Evans et al.

[11] Patent Number: 5,703,253
[45] Date of Patent: Dec. 30, 1997

[54] ETHYLENE OXIDE CATALYST AND PROCESS

[75] Inventors: Wayne E. Evans, Richmond, Tex.; Carolus Matthias Anna Maria Mesters, Amsterdam, Netherlands

[73] Assignee: Shell Oil Company, Houston, Tex.

[21] Appl. No.: 721,643

[22] Filed: Sep. 26, 1996

Related U.S. Application Data

[62] Division of Ser. No. 366,069, Dec. 29, 1994, Pat. No. 5,597,773, which is a continuation of Ser. No. 176,044, Dec. 30, 1993, Pat. No. 5,418,202.

[51] Int. Cl.$^6$ .................................................. C07D 301/10
[52] U.S. Cl. ........................ 549/536; 502/308; 502/319; 502/321; 502/344; 502/348; 502/349
[58] Field of Search .............................................. 549/536

[56] References Cited

U.S. PATENT DOCUMENTS

| | | | |
|---|---|---|---|
| 4,459,372 | 7/1984 | Arena | 502/351 |
| 4,908,343 | 3/1990 | Bhasin | 502/218 |
| 5,057,481 | 10/1991 | Bhasin | 502/208 |
| 5,418,202 | 5/1995 | Evans et al. | 502/348 |

FOREIGN PATENT DOCUMENTS

| | | |
|---|---|---|
| 266015 | 10/1987 | European Pat. Off. . |
| J7 8012-489 | 9/1969 | Japan . |

*Primary Examiner*—C. Warren Ivy
*Assistant Examiner*—Lyman H. Smith
*Attorney, Agent, or Firm*—Y. Grace Tsang

[57] ABSTRACT

This invention relates to ethylene oxide catalyst for the vapor phase production of ethylene oxide from ethylene and oxygen prepared by impregnating a porous, refractory support having a surface area ranging from about 0.05 to about 10 $m^2/g$ with a solubilized catalytically effective amount of silver, a solubilized promoting amount of alkali metal, a solubilized promoting amount of rhenium, and a solubilized promoting amount of hafnium metal, wherein the Group IVB metal is provided in the form of Group IVB oxycation-containing salts. The catalyst provide substantial initial activity improvement as well as long term selectivity and activity stability improvement over prior art rhenium promoted catalyst, without any loss of initial selectivity advantage.

15 Claims, No Drawings

ETHYLENE OXIDE CATALYST AND PROCESS

This is a division of application Ser. No. 08/366,069, filed Dec. 29, 1994 now U.S. Pat. No. 5,597,773, which is a continuation of application Ser. No. 08/176,044 filed Dec. 30, 1993 now U.S. Pat. No. 5,418,202.

FIELD OF THE INVENTION

This invention relates to supported silver-based catalysts suitable for the preparation of ethylene oxide and to the use of the catalysts for the preparation of ethylene oxide. The catalysts comprise a promoting amount of Group IVB metal provided in the form of group IVB metal oxycation-containing compound(s).

BACKGROUND OF THE INVENTION

Supported silver catalysts have long been used in the conversion of ethylene and oxygen to ethylene oxide. The use of small amounts of the alkali metals, K, Rb and Cs, were noted as useful promoters in supported silver catalysts in U.S. Pat. No. 3,962,136, issued Jun. 8, 1976 and U.S. Pat. No. 4,010,115, issued Mar. 1, 1977.

Rhenium was noted as being effective in improving selectivity of alkali metal doped silver based catalyst supported on a porous refractory support in U.S. Pat. No. 4,761,394 issued Aug. 2, 1988 and in U.S. Pat. No. 4,833,261 issued May 23, 1989. U.S. Pat. No. 4,766,105 issued Aug. 23, 1988, U.S. Pat. No. 4,820,675 issued Apr. 11, 1989, and U.S. Pat. No. 4,808,738 issued Feb. 28, 1989 further disclose the use of sulfur, Mo, W, Cr as rhenium co-promotor for such rhenium promoted catalyst.

These rhenium promoted catalysts exhibit exceptionally high selectivity as compared to conventional rhenium free catalysts. However, it exhibits lower initial activities and faster activity decline rate than that of the conventional rhenium free catalysts.

In commercial operation, reactor temperature is gradually increased to maintain an acceptable ethylene oxide production rate as catalyst activity diminishes. Ethylene oxide catalysts are generally run until the upper temperature limit of the unit is reached. Also, acceptable selectivity must be maintained throughout the life of the catalyst. Therefore, the lifespan of a catalyst depends on five factors: 1) initial activity, 2) activity decline rate, 3) upper temperature limit of the reactor, 4) initial selectivity, and 5) selectivity decline rate.

As a result of the low initial reactivity and faster activity decline rate, a reactor loaded with rhenium promoted catalyst has to be operated at a higher temperature at the initial stage and the temperature "window of operation" prior to reaching the metallurgical limits of the commercial reactor is considerably narrower. Consequently, the commercial lifespan of rhenium promoted catalyst is shorter than a conventional catalyst. The lifespan of the rhenium promoted catalyst is especially shortened in commercial reactors that have restrictive temperature limitations, most notably in the increasingly popular water cooled reactors.

Increasing initial catalytic activity as well as holding activity and selectivity stability for rhenium promoted catalyst, while maintaining the selectivity advantage, is believed to be one of the most critical issues for the development of an improved high selectivity rhenium promoted catalyst with long catalyst life.

Some references in the art have suggested the use of group IVB metals as an ingredient in the silver based ethylene oxide catalyst. U.S. Pat. No. 4,908,343 issued Mar. 13, 1990 and U.S. Pat. No. 5,057,481 issued Oct. 15, 1991 disclosed cesium promoted, silver based supported catalysts containing oxyanion of group 3b through group 7b, including, among a large group of oxyanions, titanate and zirconate.

Japanese patent application 78,012,489, published May 1, 1978, disclosed an olefin oxides silver based catalyst containing group IV element. The catalyst is not supported by a porous support and does not contain rhenium.

European patent application 266,015 published May 4, 1988 disclosed a silver based ethylene oxide catalyst containing rhenium metal promoter and at least one further metal promoters. A large number of metals, including group IVB metals, were listed as suitable further metal promoters. The metal promoters are believed to be present as oxidic compounds in numerous forms listed, including oxides, hydroxides, nitrates, sulfates, carboxylates, carbonates, bicarbonates, oxyhalides, etc,. However, there was no mention as to which oxidic form provides better catalytic performance.

It has now been found, that the addition of group IVB oxycation-containing salts to a silver based ethylene oxide catalyst, having a promoting amount of alkali metal and promoting amount of rhenium, provides substantial improvement in both initial activity and long term stability in selectivity, while the high initial selectivity advantage of prior art rhenium promoted catalysts is maintained. Furthermore, the activity advantage is maintained throughout the catalyst life time.

SUMMARY OF THE INVENTION

This invention relates to an ethylene oxide catalyst for the vapor phase production of ethylene oxide from ethylene and oxygen prepared by impregnating a porous, refractory support having a surface area ranging from about 0.05 to about 10 $m^2/g$ with a solubilized catalytically effective amount of silver, a solubilized promoting amount of alkali metal, a solubilized promoting amount of rhenium, and a solubilized promoting amount of Group IVB metal, wherein the Group IVB metal is provided in the form of group IVB metal oxycation-containing compound(s).

The catalyst provides substantial improvement in both initial activity and long term stability in selectivity over prior art catalysts, while the high initial selectivity advantage of prior art rhenium promoted catalysts is maintained. Furthermore, the activity advantage is maintained throughout the catalyst life time.

Description of the Embodiments

The Catalyst

The catalysts of the instant invention comprise a catalytically effective amount of silver, a promoting amount of alkali metal, a promoting amount of Group IVB metal provided in the form of Group IVB oxycation-containing compound(s), a promoting amount of rhenium supported on a porous, refractory support. Other promoters in promoting amounts may be optionally present such as rare earths, magnesium, rhenium co-promoters selected from chromium, molybdenum, tungsten and mixture thereof.

In broad general term, the catalysts of the instant invention are prepared by impregnating porous refractory supports with silver ions or compound(s), complex(es) and/or salt(s) dissolved in a suitable solvent sufficient to cause deposition on the support of a promoting amount of silver; the thus impregnated carrier is then separated from the solution and the deposited silver compound is reduced to metallic silver. Also deposited on the support either prior to, coincidentally with, or subsequent to the deposition of the silver will be a promoting amount of suitable ions, or compound(s) and/or salts(s) of alkali metal dissolved in a suitable solvent. Also deposited on the carrier either prior to, coincidentally with, or subsequent to the deposition of the silver and/or alkali metal will be promoting amount of suitable rhenium ion(s) or compound(s), complex(es) and/or salt(s) dissolved in an appropriate solvent. Also deposited on the carrier prior to, coincidentally with, or subsequent to the deposition of the silver and/or alkali metal and/or rhenium will be promoting amount of group IVB metal(s) provided in the form of oxycation-containing complexes or compound(s) and/or salt(s) thereof dissolved in a suitable solvent.

The support or carrier employed in the catalysts of the present invention in its broadest aspect is selected from the larger number of conventional, porous refractory catalyst carriers or support materials which are considered relatively inert in the presence of the ethylene oxidation feeds, products and reaction conditions. Such conventional materials are known to those skilled in the art and may be of natural or synthetic origin and preferably are of a macroporous structure, i.e., a structure having a surface area below about 10 m$^2$/g and preferably below about 3 m$^2$/g. Particularly suitable supports are those of aluminous composition. Preferred supports comprise the aluminous materials, in particular those comprising alpha alumina. In the case of alpha alumina-containing supports, preference is given to those having a specific surface area as measured by the B.E.T. method of from about 0.03 m$^2$/g to about 10 m$^2$/g, preferably from about 0.05 m$^2$/g to about 5 m$^2$/g, more preferably from about 0.1 m$^2$/g to about 3 m$^2$/g, and a water pore volume as measured by conventional water absorption techniques of from about 0.1 to about 0.75 cc/g by volume, preferably from about 0.3 to about 0.5 cc/g. The B.E.T. method for determining specific surface area is described in detail in Brunauer, S., Emmet, P. Y. and Teller, E., *J. Am. Chem. Soc.*, 60, 309–16 (1938). Suitable alpha alumina-containing supports are particularly described in U.S. Pat. No. 4,761,394, issued Aug. 2, 1988, which is incorporated by reference herein. Suitable manufacturers of carriers include Norton Company and United Catalysts, Inc. (UCI).

A particularly preferred support suitable for use in the present invention comprises alpha alumina based carrier having a crush strength of at least about 5 pounds and a settled packing density of at least about 30 pounds/cubic foot which comprises first and second alpha alumina components with a first alpha alumina component in the form of particles having a median crystallite size of from about 0.4 to about 4 microns providing from about 95% to about 40% of the total weight of alpha alumina in the carrier and a second alpha alumina component generated in situ by a sol-gel process and providing the balance of the alpha alumina in the carrier. In a still more particularly preferred support, it further comprises from about 0.05% by weight to about 1% by weight of titania, based on the weight of alumina in the carrier.

The support, irrespective of the character of the support or carrier used, is preferably shaped into particles, chunks, pieces, pellets, rings, spheres, wagon wheels, and the like of a size suitable for use in fixed bed reactors. Conventional commercial fixed bed reactors are typically in the form of a plurality of parallel elongated tubes (in a suitable shell) approximately 0.7 to 2.7 inches O.D. and 0.5 to 2.5 inches I.D. and 15–45 feet long filled with catalyst. In such reactors, it is desirable to use a support formed into a rounded shape, such as, for example, spheres, pellets, rings, tablets and the like, having diameters from about 0.1 inch to about 0.8 inch.

The catalysts of the present invention are prepared by a technique in which the alkali metal promoters, rhenium metal promoters, Group IVB metal promoters in the form of soluble salts and/or compounds are deposited on the catalyst and/or support prior to, simultaneously with, or subsequent to the deposition of the silver and each other. The preferred method is to deposit silver, rhenium metal, alkali metal and Group IVB metal oxycation-containing complex promoters simultaneously on the support, that is, in a single impregnation step, although it is believed that the individual or concurrent deposition of the alkali metal and Group IVB metal oxycation-containing complex, prior to and/or subsequent to the deposition of the silver would also produce suitable catalysts.

Promoting amounts of group IVB metal, provided in the form of oxycation-containing complex(es), or mixtures thereof are deposited on a porous support using a suitable solution prior to, coincidentally with, or subsequent to the deposition of the silver and/or alkali metal and/or rhenium. As used herein, the term "Group IVB metal" and cognates thereof refers to the Group IVB metals, according to the CAS version of the Periodic Table, selected from the group consisting of titanium, zirconium and hafnium and mixtures thereof. As a preferred embodiment of the present invention, promoting amounts of hafnium oxycation-containing compound(s) or zirconium oxycation-containing compound(s), or mixtures thereof are firsts dissolved in a suitable solution prior to being deposited on the carrier. As a particularly preferred embodiment, promoting amounts of hafnium oxycation-containing compound(s) are used. Without intending to limit the scope of the invention, an oxycation-containing compound of Group IVB metals comprises an "oxycation" moiety which is an assemblage of atoms comprising at least one Group IVB metal atom(s) covalently bonded to at least one oxygen atom(s), and this assemblage of atoms comprising at least one Group IVB metal atoms(s) covalently bonded to at least one oxygen atom(s) carries a positive charge. Illustrative and non-limiting examples of Group IVB metal oxycations include $HfO^{+2}$, $ZrO^{+2}$, $TiO^{+2}$, $[Zr_4(OH)_8(H_2O)_{16}]^{+8}$, etc. This "oxycation" moiety can be bound to other atoms/ions such as chloride, carbonate, nitrate, etc. Without intending to limit the scope of the invention, examples of suitable compounds of Group IVB metal oxycation-containing compound(s) include oxyhalide, oxycarbonate, oxynitrate of hafnium and/or zirconium, and the hydrates thereof, i.e. $HfOCl_2$, $HfOCO_3$, $HfO(NO_3)_2$, $ZrOCl_2$, $ZrOCO_3$, $ZrO(NO_3)_2$, $HfOCl_2.8H_2O$, $ZrOCl_2.8H_2O$, etc. Optionally, the Group IVB oxycation-containing compound(s) can be further complexed or coordinated with other ligands or complexing agents such as amine containing ligands. As a preferred embodiment of the present invention, the Group IVB oxycation-containing compound(s) are dissolved in an aqueous solution containing ammonium carbonate solution before being deposited on the support. Without intending to limit the scope of the invention, it is believed that ammonium carbonate facilitates in solubilizing the Group IVB oxycation-containing-containing compounds in the aqueous solution. The promoting amount of Group IVB metal utilized will depend on several variables, such as, for example, the surface area and pore structure and surface chemical properties of the carrier used, the silver content of the catalyst, the amount of rhenium promoter, the amount of alkali metal promoter and the particular ions used in conjunction with the Group IVB metal cation/complex, optional co-promoters. The amount of Group IVB metal deposited upon the support generally lies between 0.01 micromoles and about 10 micromoles per gram of the total catalyst, and preferably between about 0.05 micromoles and about 5 micromoles per gram of the total catalyst. Most preferably between about 0.1 micromoles and about 2 micromoles per gram of the total catalyst.

After being deposited on the catalyst carrier, the group IVB metal promoters, which were initially added to the impregnation solution as oxycation-containing complexes, may present on the catalysts in the form of oxycation-containing complexes, cations (ions) or compounds of complexes or surface compounds or surface complexes rather than as the free Group IVB metallic elements, although for convenience purposes in this specification and claims they are referred to as "Group IVB metal" or "Group IVB metal promoters" even though they are not present on the catalyst as metallic elements. For purposes of convenience, the amount of alkali metal deposited on the support or present on the catalyst is expressed as the metal.

Promoting amounts of alkali metal or mixtures of alkali metal are deposited on a porous support using a suitable solution. Although alkali metals exist in a pure metallic state, they are not suitable for use in that form. They are used as ions or compounds of alkali metals dissolved in a suitable solvent for impregnation purposes. The carrier is impregnated with a solution of alkali metal promoter ions, salt(s) and/or compound(s) before, during or after impregnation of the silver and/or Group IVB metal oxycation-containing ions or salt(s), complex(es), and/or compound(s) has taken place. An alkali metal promoter may even be deposited on the carrier after reduction to metallic silver has taken place.

The promoting amount of alkali metal utilized will depend on several variables, such as, for example, the surface area and pore structure and surface chemical properties of the carrier used, the silver content of the catalyst, the amount of rhenium promoter, the amount of Group IVB metal promoter and the particular ions used in conjunction with the alkali metal cation, optional co-promoters. The amount of alkali metal promoter deposited upon the support or present on the catalyst generally lies between about 10 parts per million and about 3000 parts per million, preferably between about 15 parts per million and about 2000 parts per million and more preferably, between about 20 parts per million and about 1500 parts per million by weight of total catalyst. Most preferably, the amount ranges between about 50 parts per million and about 1000 parts per million by weight of the total catalyst. The degree of benefit obtained within the above-defined limits will vary depending upon particular properties and characteristics, such as, for example, reaction conditions, catalyst preparative techniques, surface area and pore structure and surface chemical properties of the carrier utilized, silver content of the catalyst, and other compounds, cations or anions present in addition to alkali metal ions, and the above-defined limits were selected to cover the widest possible variations in properties and characteristics. The effects of these variation in properties are readily determined by experimentation. The alkali metal promoters are present on the catalysts in the form of cations (ions) or compounds of complexes or surface compounds or surface complexes rather than as the extremely active free alkali metals, although for convenience purposes in this specification and claims they are referred to as "alkali metal" or "alkali metal promoters" even though they are not present on the catalyst as metallic elements. For purposes of convenience, the amount of alkali metal deposited on the support or present on the catalyst is expressed as the metal. Without intending to limit the scope of the invention, it is believed that the alkali metal compounds are oxidic compounds. More particularly, it is believed that the alkali metal compounds are probably in the form of mixed surface oxides or double surface oxides or complex surface oxides with the aluminum of the support and/or the silver of the catalyst, possibly in combination with species contained in or formed from the reaction mixture, such as, for example, chlorides or carbonates or residual species from the impregnating solution(s).

In a preferred embodiment, at least a major proportion (greater than 50%) of the alkali metals are selected from the group consisting of lithium, potassium, cesium, and mixtures thereof. As used herein, the term "alkali metal" and cognates thereof refers to the alkali metals selected from the group consisting of lithium, sodium, potassium, rubidium, cesium and mixtures thereof. As used herein, the term "mixtures of alkali metals" or cognates of these terms refers to the use of two or more of the alkali metals, as appropriate, to provide a promoting effect. Non-limiting examples include cesium plus rubidium, cesium plus potassium, cesium plus sodium, cesium plus lithium, cesium plus rubidium plus sodium, cesium plus potassium plus sodium, cesium plus lithium plus sodium, cesium plus rubidium plus potassium plus sodium, cesium plus rubidium plus potassium plus lithium, cesium plus potassium plus lithium and the like. A preferred alkali metal promoter is cesium. A particularly preferred alkali metal promoter is cesium plus at least one additional alkali metal. The additional alkali metal is preferably selected from sodium, lithium and mixtures thereof, with lithium being preferred.

It should be understood that the amounts of alkali metal or Group IVB metal promoters on the catalysts are not necessarily the total amounts of these metals present in the catalyst. Rather, they are the amounts of alkali metal or Group IVB promoters which have been added to the catalyst by impregnation with a suitable solution of ions, salts and/or compounds and/or complexes of alkali metals or Group IVB metals. These amounts do not include amounts of alkali metals or Group IVB metals which are locked into the support, for example, by calcining, or are not extractable in a suitable solvent such as water or lower alkanol or amine or mixtures thereof and do not provide a promoting effect. It is also understood that a source of the alkali metal or Group IVB metal promoter ions, complexes, salts and/or compounds used to promote the catalyst may be the carrier. That is, the carrier may contain extractable amounts of alkali metal or Group IVB metal that can be extracted with a suitable solvent, such as water or lower alkanol, thus preparing an impregnating solution from which the alkali metal or Group IVB metal ions, complexes, salts and/or compounds are deposited or redeposited on the support.

Other promoters and co-promoters can be used in conjunction with the silver, rhenium promoters, alkali metal promoters and Group IVB metal promoters. Non-limiting examples of other promoters include molybdate, sulfate, tungstate and chromate (see U.S. Pat. No. 4,766,105, issued Aug. 23, 1988); fluoride anion, oxyanions of Groups 3b to 6b (see U.S. Pat. No. 5,102,848, issued Apr. 7, 1992); (i) oxyanions of an element selected from Groups 3 through 7b and (ii) alkali(ne) metal salts with anions of halides, and oxyanions selected from Groups 3a to 7a and 3b through 7b (see U.S. Pat. No. 4,908,343, issued Mar. 13, 1990). It is noted that sulfate anion when deposited in the amount of about 1 to 2 micromoles per gram of total catalyst prepared by depositing thereon about 1–2 micromoles of rhenium, about 5.0 micrograms of lithium and about 0.5–1.0 micromoles of hafnium oxyhalide and about 500 to 700 micromoles of cesium per gram of the total catalyst does not necessary enhance the activity or selectivity of the present catalyst. However, it is believed that sulfate anion present in different amounts, or when combined with other promoters or copromoters and/or when combined promoters or copromoters in different amounts might still be beneficial.

The carrier is also impregnated with rhenium ions, salt(s), compound(s) and/or complex(es) prior to, coincidentally with, or subsequent to the deposition of the silver and/or alkali metal and/or Group IV metal. The amount of rhenium promoter preferably present on the catalyst generally lies between about 0.1 to about 10, more preferably between about 0.2 to about 5 micromoles (basis metal) per gram of total catalyst.

Suitable rhenium promoters, the form of the rhenium metal on the catalyst, the promoting effects, etc. are described in U.S. Pat. No. 4,761,394, issued Aug. 2, 1988, which is herein incorporated by reference.

As used herein, the term "promoting amount" of a certain component of a catalyst refers to an amount of that component which works effectively to provide an improvement in one or more of the catalytic properties of that catalyst when compared to a catalyst not containing said component. Examples of catalytic properties include, inter alia, operability (resistance to runaway), selectivity, activity, conversion, stability and yield. It is understood by one skilled in the art that one or more of the individual catalytic properties may be enhanced by the "promoting amount" while other catalytic properties may or may not be enhanced and may even be diminished. It is further understood that different catalytic properties may be enhanced at different operation conditions. For example, a catalyst having enhanced selectivity at one set of operating conditions may be operated at a different set of conditions wherein the improvement shows up in the activity rather that the selectivity and an operator of an ethylene oxide plant will intentionally change the operation conditions in order to take advantage of certain catalytic properties even at the expense of other catalytic properties in order to maximize profits by taking into account feedstock costs, energy costs, by-product removal costs and the like. For example, the particular combination of silver, support, rare earth promoter, alkali metal promoter, rhenium promoter and optionally, rhenium co-promoter of the instant invention will provide an improvement in one or more catalytic properties over the same combination of silver, support, alkali metal promoter, rhenium promoter and optionally, rhenium co-promoter and no rare earth promoter.

As used herein, the term "catalytically effective amount of silver" refers to an amount of silver that provides a measurable conversion of ethylene and oxygen to ethylene oxide.

Generally, the carrier is contacted with a silver salt, a silver compound, or a silver complex which has been dissolved in an aqueous solution, so that the carrier is impregnated with said aqueous solution; thereafter the impregnated carrier is separated from the aqueous solution, e.g., by centrifugation or filtration and then dried. The thus obtained impregnated carrier is heated to reduce the silver to metallic silver. It is conveniently heated to a temperature in the range of from about 50° C. to about 600° C., during a period sufficient to cause reduction of the silver salt, compound or complex to metallic silver and to form a layer of finely divided silver, which is bound to the surface of the carrier, both the exterior and pore surface. Air, or other oxidizing gas, reducing gas such as hydrogen containing gas, an inert gas or mixtures thereof may be conducted over the carrier during this heating step. As a specific embodiment of the present invention, the reduction is conducted in the presence of air. As another specific embodiment of the present invention, the said reduction is conducted by contacting the impregnated carrier with a gas comprising hydrogen, or an inert gas containing at least about 4 volume percent hydrogen. As still another specific embodiment of the present invention, the impregnated carrier is first subjected to a calcination procedure wherein a gas, such as air, oxygen-depleted air, inert gases such as nitrogen, argon, helium, etc. or any mixture thereof, is passed over or through the impregnated carrier at a temperature of about 250° to 350° C. for about 2–4 hours, and then subject to reduction under a gas comprising at least 4 volume percent hydrogen.

There are several known methods to add the silver to the carrier or support. The carrier may be impregnated with an aqueous solution containing silver nitrate dissolved therein, and then dried, after which drying step the silver nitrate is reduced with hydrogen or hydrazine. The carrier may also be impregnated with an ammoniacal solution of silver oxalate or silver carbonate, and then dried, after which drying step the silver oxalate or silver carbonate is reduced to metallic silver by heating, e.g., to about 600° C. Specific solutions of silver salts with solubilizing and reducing agents may be employed as well, e.g., combinations of the vicinal alkanolamines, alkyldiamines and ammonia. One such example of a solution of silver salts comprises an impregnating solution comprising a silver salt of a carboxylic acid, an organic amine alkaline solubilizing/reducing agent, and an aqueous solvent.

Suitable carboxylic acid silver salts include silver carbonate and the silver salts of mono- and polybasic carboxylic and hydroxycarboxylic acids of up to about 16 carbon atoms. Silver carbonate and silver oxalate are particularly useful silver salts, with silver oxalate being most preferred.

Suitable organic amine silver-solubilizing/reducing agents include lower alkylenediamines of from 1 to 5 carbon atoms, mixtures of a lower alkanolamine of from 1 to 5 carbon atoms with a lower alkylenediamine of from 1 to 5 carbon atoms, as well as mixtures of ammonia with lower alkanolamines or lower alkylenediamines for from 1 to 5 carbons. Four groups of organic amine solubilizing/reducing agents are particularly useful. The four groups include vicinal alkylenediamines of from 2 to 4 carbon atoms, mixtures of (1) vicinal alkanolamines of from 2 to 4 carbon atoms and (2) vicinal alkylenediamines of from 2 to 4 carbon atoms, mixtures of vicinal alkylenediamines of from 2 to 4 carbon atoms and ammonia, and mixtures of vicinal alkanolamines of from 2 to 4 carbon atoms and ammonia. These solubilizing/reducing agents are generally added in the amount of from about 0.1 to about 10 moles per mole of silver present.

Particularly preferred solubilizing/reducing agents are ethylenediamine, ethylenediamine in combination with ethanolamine, ethylenediamine in combination with ammonia, and ethanolamine in combination with ammonia, with ethylenediamine being most preferred. Ethylenediamine in combination with ethanolamine gives comparable results, but it is believed that impurities present in certain commercially available ethanolamine preparations can produce inconsistent results.

When ethylenediamine is used as the sole solubilizing/reducing agent, it is necessary to add amounts of the amine in the range of from about 0.1 to about 5.0 moles of ethylenediamine per mole of silver.

When ethylenediamine and ethanolamine together are used as the solubilizing/reducing agent, it is suitable to employ from about 0.1 to about 3.0 moles of ethylenediamine per mole of silver and from about 0.1 to about 2.0 moles of ethanolamine per mole of silver.

When ethylenediamine or ethanolamine is used with ammonia, it is generally useful to add at least about two moles of ammonia per mole of silver and very suitable to add from about 2 to about 10 moles of ammonia per mole of silver. The amount of ethylenediamine or ethanolamine employed then is suitably from 0.1 to 2.0 moles per mole of silver.

One method of preparing the silver containing catalyst can be found in U.S. Pat. No. 3,702,259, issued Nov. 7, 1972, incorporated by reference herein. Other methods for preparing the silver-containing catalysts which in addition contain higher alkali metal promoters can be found in U.S. Pat. No. 4,010,115, issued Mar. 1, 1977; and U.S. Pat. No. 4,356,312, issued Oct. 26, 1982; U.S. Pat. No. 3,962,136, issued Jun. 8, 1976 and U.S. Pat. No. 4,012,425, issued Mar. 15, 1977, all incorporated by reference herein. Methods for preparing silver-containing catalysts containing higher alkali metal and rhenium promoters can be found in U.S. Pat. No. 4,761,394, issued Aug. 2, 1988, which is incorporated by reference herein, and methods for silver-containing catalysts containing higher alkali metal and rhenium promoters and a rhenium co-promoters can be found in U.S. Pat. No. 4,766,105, issued Aug. 2, 1988, which is incorporated herein by reference. Methods for preparing silver-containing catalysts with a variety of different promoters are found in U.S. Pat. No. 4,908,343, issued Mar. 13, 1990 and U.S. Pat. No. 5,057,481, issued Oct. 15, 1991, both incorporated herein by reference.

A particularly preferred process of impregnating the carrier consists of impregnating the carrier with an aqueous solution containing a silver salt of a carboxylic acid, an organic amine, a salt of cesium, a salt of hafnium oxychloride, and a salt of rhenium dissolved therein. Silver oxalate is a preferred silver salt. It can be prepared by reacting silver oxide (slurry in water) with (a) a mixture of ethylenediamine and oxalic acid, or (b) oxalic acid and then ethylenediamine, which latter is preferred, so that an aqueous solution of silver oxalate-ethylenediamine complex is obtained, to which solution is added a certain amount of cesium compound, rhenium compound and hafnium oxycation-containing salt. While addition of the amine to the silver oxide before adding the oxalic acid is possible, it is not preferred since it can give rise to solutions which are unstable or even explosive in nature. Other diamines and other amines, such as ethanolamine, may be added as well. The impregnated carriers are then heated to a temperature between about 50° C. and about 600° C., preferably between about 75° C. and about 400° C. to evaporate the liquid and produce a metallic silver.

In general terms, the impregnation process comprises impregnating the support with one or more solutions comprising silver, alkali metal, rhenium, Group IVB metal and optional other promoters. As used in the instant specification and claims, the terminology "impregnating the support with one or more solutions comprising silver, alkali metal, rhenium, Group IVB metal and optional other promoters" and similar or cognate terminology means that the support is impregnated in a single or multiple impregnation with one solution containing silver, alkali metal, rhenium, group IVB metal and optional other promoters in differing amounts; or in multiple impregnations with two or more solutions, wherein each solution contains at least one component selected from silver, alkali metal, group IVB metal, rhenium and optional other promoter(s), with the proviso that all of the components of silver, alkali metal, rhenium and group IVB metal will individually be found in at least one of the solutions. The concentration of the silver (expressed as the metal) in the silver-containing solution will range from about 1 g/l up to the solubility limit when a single impregnation is utilized. The concentration of the alkali metal (expressed as the metal) will range from about $1\times10^{-3}$ g/l up to about 12 g/l and preferably, from about $10\times10^{-3}$ g/l to about 12 g/l when a single impregnation step is utilized. The concentration of the rhenium will range from about $8\times10^{-2}$ g/l up to about 8 g/l. The concentration of the group IVB metal will range from about $5\times10^{-2}$ g/l up to about 5 g/l. Concentrations selected within the above noted ranges will depend upon the pore volume of the catalyst, the final amount desired in the final catalyst and whether the impregnation is single or multiple. Appropriate concentrations can be readily determined by routine experimentation.

It is observed that independent of the form in which the silver is present in the solution before precipitation on the carrier, the term "reduction to metallic silver" is used, while in the meantime often decomposition by heating occurs. We prefer to use the term "reduction", since $Ag^+$ ion is converted into a metallic Ag atom. Reduction times may generally vary from about 0.5 minute to about 8 hours, depending on the circumstances. The amount of silver deposited on the support or present on the support is to be a catalytically effective amount of silver, i.e., an amount that provides a measurable conversion of ethylene and oxygen to ethylene oxide. Preferably this amount will range from about 1 to about 30 percent by weight of the total catalyst, more preferably from about 1 to about 25 percent by weight of the total catalyst, and even more preferably from about 5 to about 20 percent by weight of the total catalyst. The upper and lower limit of preferred silver concentrations can be suitably varied, depending upon the particular catalytic properties or effect desired or other variables involved.

The Group IVB promoted rhenium containing silver catalysts according to the present invention have been shown to provide substantial initial activity improvement as well as long term selectivity stability improvement, while without any loss of initial selectivity advantage of prior art rhenium promoted catalyst. The activity advantage is maintained throughout the catalyst life.

Process for Ethylene Oxide Production

In commercial operations, ethylene and oxygen are converted to ethylene oxide in an ethylene oxide reactor which comprises a large fixed tube sheet heat exchanger containing several thousand tubes filled with catalyst. A coolant is used on the shell side of the reactor to remove the heat of reaction. Coolant temperatures are frequently utilized as an indication of catalyst activity, high coolant temperatures corresponding to lower catalyst activities. In the vapor phase reaction of ethylene with oxygen to produce ethylene oxide, the ethylene is present in at least a double amount (on a mole basis) compared with oxygen, but is often much higher. Therefore the conversion is calculated according to the molar percentage of oxygen which has been used in the reaction. The oxygen conversion is dependent on the reaction temperature which latter is a measure of the activity of the catalyst employed. The value $T_{40}$ indicates the temperature at 40 mole percent conversion of the oxygen in the reactor and the value T is expressed in °C. This temperature is generally higher when the conversion of oxygen is higher. Moreover, this temperature is strongly dependent on the employed catalyst and the reaction conditions. The selectivity (to ethylene oxide) indicates the molar amount of ethylene oxide in the reaction product compared with the total molar amount ethylene converted. Herein the selectivity is indicated as $S_{40}$, which means the selectivity at 40 molar percent oxygen conversion. The selectivity of silver based ethylene oxide catalysts can decrease over a period of time of usage. When comparing the selectivity performance of various silver-based ethylene oxide catalysts, it is important that the selectivity value be measured at approximately the same period of time of usage under the same or similar reaction conditions. As used herein, "initial selectivity" will refer to the selectivity of ethylene oxide catalysts when measured at a given constant oxygen conversion level of 40% at a gas hourly space velocity of approximately 3300 and when measured after the catalyst has been placed On stream for about 16±4 hours. Unless otherwise noted, all selectivities that are provided in the examples provided herein are initial selectivities. Alternatively, severity can be expressed as the level of EO production. For example, $T_{1.5}$ is defined as the temperature required to produce an outlet EO level of 1.5%. $S_{1.5}$ is defined as the selectivities at 1.5% EO production.

The conditions for carrying out an ethylene oxidation reaction in the presence of the silver catalysts according to the present invention broadly comprise those already described in the prior art. This applies, for example, to suitable temperatures, pressures, residence times, diluent materials, such as nitrogen, carbon dioxide, steam, argon, methane or other saturated hydrocarbons, presence of moderating agents to control the catalytic action, for example, 1,2-dichloroethane, vinyl chloride, ethyl chloride or chlorinated polyphenyl compounds, the desirability of employing recycle operations or applying successive conversions in different reactors to increase the yields of ethylene oxide, and any other special conditions which may be selected in processes for preparing ethylene oxide. Pressures in the range of from atmospheric to 35 bar are generally employed. Higher pressures are, however, by no means excluded. Molecular oxygen employed as reactant can be obtained from conventional sources. The suitable oxygen charge may consist essentially of relatively pure oxygen, a concentrated oxygen stream comprising oxygen in major amount with lesser amounts of one or more diluents, such as nitrogen and argon, or another oxygen-containing stream, such as air. It is therefore evident that the use of the present silver catalysts in ethylene oxidation reactions is in no way limited to the use of specific conditions among those which are known to be effective. For purposes of illustration only, the following table shows the range of conditions that are often used in current commercial ethylene oxide reactor units and which are also suitable for the instant process.

TABLE I

| *GHSV | 1550–10,000 |
| Inlet pressure | 150–400 psig |
| Inlet Feed | |
| ethylene | 10–40% |
| $O^2$ | 3–12% |
| $CO^2$ | 0.1–40% |
| ethane | 0–3% |
| Argon and/or methane and/or nitrogen diluent chlorohydrocarbon moderator | 0.3–20 ppmv total |
| Coolant temperature | 180–315° C. |
| Catalyst temperature | 180–325° C. |
| $O^2$ conversion level | 10–60% |
| EO Production (Work Pate) | 2–16 lbs. EO/cu. ft. catalyst/hr. |

*Liters of gas at standard temperature and pressure passing over one liter of packed catalyst per hour.

In a preferred application of the silver catalysts according to the present invention, ethylene oxide is produced when an oxygen-containing gas is contacted with ethylene in the presence of the present catalysts at a temperature in the range of from about 180° C. to about 330° C. and preferably about 200+ C. to about 325° C.

Process for Epoxidation of Olefins

While the catalysts of the present invention are preferably used to convert ethylene and oxygen to ethylene oxide, as a specific embodiment of the present invention, olefins having no allylic hydrogens can be oxidized using the silver catalysts of the present invention to produce a high selectivity of epoxide derivatives thereof by contacting the olefin feed with an oxygen-containing gas in the presence of an organic halide and the silver catalyst described above under defined oxidation conditions.

The process for the selective epoxidation of olefins having no allylic hydrogens comprises contacting the feed olefin, preferably an olefin having at least 4 carbon atoms, with a sufficient quantity of an oxygen-containing gas so as to maintain the molar ratio of olefin to oxygen in the range of about 0.01 up to about 20, in the presence of an organic halide and a silver catalyst at a reaction pressure in the range of about 0.1 up to about 100 atmospheres and a temperature in the range of about 75° up to about 325° C. for a reaction time sufficient to obtain olefin conversions per pass in the range of about 0.1 up to about 75 mole percent.

Olefins contemplated for use in this oxidation process are those which satisfy the following structural formula:

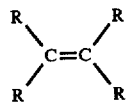

wherein each R is independently selected from the group consisting of:
(a) hydrogen,
(b) aryl and substituted aryl groups having in the range of 7 up to 20 carbon atoms,
(c) alkyl groups of the formula:

where each R' is independently:

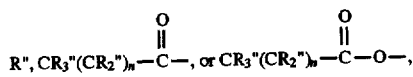

where R" is H, $C_1$–$C_{10}$ alkyl or substituted alkyl, an aryl or substituted aryl group having 6 up to 20 carbon atoms, and n is a whole number from 0–12;
(d) $CR_3"$—$(CR_2")_x$—O—, where x is a whole number from 1–12;
(e)

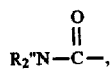

(f) $R_2"N$—;
(g) $R"S$—;
(h) $CR_2"=CR"$—$(CR"=CR")_y$,
where y is an integer from 0–20; and (i)

where X is O, S or NR"; and m is an integer from 0–3; with the proviso that said olefin have no allylic hydrogens and that at least one R-group not be hydrogen.

Exemplary olefins which satisfy the above structural formula include butadiene, tertiary butylethylene, vinyl furan, methyl vinyl ketone, N-vinyl pyrrolidone, and the like. A presently preferred olefin for use in the practice of this process is butadiene because of its ready availability, relatively low cost, and the wide range of possible uses for the epoxide reaction product.

The epoxides produced by this process have the structural formula:

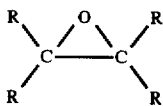

wherein each R is independently defined as set forth above. Where one or more of the R-groups contain carbon-carbon bond unsaturation, further oxidation can be carried out, thereby producing polyepoxide products.

The process is carried out by contacting the olefin to be oxidized with molecular oxygen and an organic halide under oxidation conditions, i.e. in the presence of sufficient quantities of an oxygen-containing gas to provide a molar ratio of olefin to oxygen in the range of about 0.01 up to about 20, and in the presence of about 0.1 up to about 1000 parts per million (by volume of total feed) of organic halide. Preferred quantities of organic halide for use in the practice of this specific embodiment of the present invention fall within the range of about 1 up to about 100 parts per million, by volume of total feed.

While greater or lesser quantities of molecular oxygen can be employed, sufficient quantities of oxygen should be provided to insure that undesirably low levels of olefin conversion do not occur, while excessively high oxygen concentrations should be avoided to prevent the formation of explosive mixtures. Similarly, lower levels of organic halide will provide negligible effect on catalyst performance, while higher levels of organic halide would not be expected to provide any significant improvement in catalyst performance.

Suitable oxygen-containing gases include air, oxygen enriched air, substantially purified oxygen, oxygen diluted with inert gases such as $N_2$, Ar, $CO_2$, $CH_4$ and the like.

The organic halide can be added to the oxidation reaction zone in a variety of ways. For example, it can be mixed with the olefin to be oxidized and/or the oxygen-containing gas prior to contacting with the catalyst, or the organic halide can be introduced to the reaction zone separately from the feed olefin and/or the oxygen-containing gas.

Suitable reaction temperatures for this specific embodiment of the present invention fall within the range of about 75° C. up to about 325° C. At lower temperatures, the reaction proceeds so slowly as to be impractical, while at higher temperatures undesirable levels of by-products, e.g. carbon dioxide, are obtained. Preferred reaction temperatures fall within the range of about 125° C. up to about 295° C.; with temperatures in the range of about 175° C. up to about 290° C. being most preferred because selectivity to the desired epoxide falls off at temperatures significantly above about 290° C. and space-time yields are undesirably low at temperatures below about 175° C.

The reaction pressure can vary within wide ranges, with typical limits of about 0.1 up to about 100 atmospheres being chosen primarily as a function of safety, handling, equipment, and other practical considerations. Preferably, reaction pressure is maintained in the range of about 1 up to about 30 atmospheres.

Reaction times suitable for this process can vary within wide ranges. Generally, olefin, oxygen, organic halide and catalyst are maintained in contact for a time sufficient to obtain olefin conversions per pass in the range of about 0.1 up to about 75 mole percent. Preferred target olefin conversion levels per pass fall within the range of about 1 up to about 50 mole percent, while reaction times sufficient to obtain olefin conversion per pass in the range of about 5 up to about 30 mole percent are presently most preferred for efficient utilization of the reactor capacity.

Those of skill in the art recognize that the actual contact times required to accomplish the desired conversion levels can vary within wide ranges, depending on such factors as vessel size, olefin to oxygen ratios, the silver loading level on the catalyst, the presence or absence of any catalyst modifiers (and their loading levels), the amount of organic halide present in the reaction zone, the reaction temperature and pressure, and the like.

The process can be carried out in either batch or continuous mode. Continuous reaction is presently preferred since high reactor throughput and high purity product is obtained in this manner. The batch mode is satisfactorily employed when high volume of reactant throughput is not required, for example, for liquid phase reactions.

For continuous mode of reaction carried out in the gas phase, typical gas hourly space velocities (GHSV) fall within the range of about 100 up to 30,000 $hr^{-1}$. GHSV in the range of about 200 up to 20,000 $hr^{-1}$ are preferred, with GHSV in the range of about 300 up to 10,000 $hr^{-1}$ being most preferred because under such conditions the most desirable combination of feed olefin conversion and product selectivities are obtained.

When continuous mode of reaction is carried out in the liquid phase, typical liquid hourly space velocities (LHSV) employed will give contact times analogous to that obtained at the GHSV values given above. Most preferably, LHSV employed will fall in the range so as to produce the most desirable combination of feed olefin conversion levels and high product selectivity.

Recovery of the epoxide product produced can readily be carried out employing techniques well known by those of skill in the art. For example, where reaction is carried out in the continuous mode, unreacted starting material is initially separated from reaction products; and the desired product then isolated from the resulting product mixture by distillation, crystallization, extraction, or the like. Since the selectivity to the desired epoxide product is generally quite high, there are only small amounts of undesired reaction products from which to isolate the desired product.

Prior to use for oxidizing olefins having no allylic hydrogens, the silver catalysts (either before or after further treatment with promoter), are optionally calcined in an oxygen-containing atmosphere (air or oxygen-supplemented helium) at about 350° C. for about 4 hours. Following calcination, the silver catalysts are typically subjected to an activation treatment at a temperature in the range of about 300°–350° C. in an atmosphere initially containing about 2–5% hydrogen in an inert carrier such as helium or nitrogen. The hydrogen content of the activating atmosphere is gradually increased up to a final hydrogen concentration of about 20–25% at a controlled rate so that the activation temperature does not exceed 350° C. After the temperature is maintained for about 1 hour at a hydrogen concentration in the range of about 20–25%, catalyst is ready for use.

More detailed descriptions of the silver catalysts and their use in oxidizing olefins having no allylic hydrogens are found in U.S. Pat. No. 4,897,498, issued Jan. 30, 1990 and U.S. Pat. No. 5,081,096, issued Jan. 14, 1992, both of which are incorporated by reference herein.

The invention will be illustrated by the following illustrative embodiments which are provided for illustration only and are not intended to limit the scope of the instant invention.

ILLUSTRATIVE EMBODIMENTS

ILLUSTRATIVE EMBODIMENT I

The following illustrative embodiment describes typical preparative techniques for making the catalysts of the instant invention (and comparative catalysts) and the typical technique for measuring the properties of these catalysts. Catalysts A-1, A-2, A-3: Experimental Catalysts Promoted by Hf Oxycation-containing Compounds Part A Preparation of stock silver oxalate/ethylenediamine solution for use in catalyst preparation 1. Dissolve 415 g reagent-grade NaOH in 2340 deionized water. Adjust temperature to 50° C.

2. Dissolve 1699 g "spectropure" (high-purity) $AgNO_3$ in 2100 ml deionized water. Adjust temperature to 50° C.

3. Add NaOH solution slowly to $AgNO_3$ solution with stirring, maintaining temperature at 50° C. Stir for 15 minutes after addition is complete, then lower temperature to 40° C. Measure the pH, which should be greater than 10.

4. Insert clean filter wands and withdraw as much water as possible from the precipitate created in step (3) in order to remove sodium and nitrate ions. Measure the conductivity of the water removed and add back as much fresh deionized water as was removed by the filter wands. Stir for 15 minutes at 40° C. Repeat this process until the conductivity of the water removed is less than 90 micro-mho/cm. Then add back 1500 ml deionized water.

5. Add 630 g of high-purity oxalic acid dihydrate in approximately 100 g increments. Keep the temperature at 40° C. and stir to mix thoroughly. Add the last portion of oxalic acid dihydrate slowly and monitor the pH to ensure that the pH does not drop below 7.8. Aim for a pH endpoint of 8.0–8.4. Add high-purity silver oxide if necessary to achieve this endpoint.

6. Remove as much water as possible with clean filter wands. Cool the slurry of silver oxalate to 30° C. Record the weight of the slurry.

7. Add 699 g of 92% ethylenediamine (8% deionized water). Do not allow the temperature to exceed 30° C. during addition.

The above procedure yields a solution containing approximately 27–33% w silver which provides the "stock solution" used in the preparation of Catalysts A-1,2,3, B-1,2,3, C-1, 2,3,4, and the standard below.

Part B

Preparation of Impregnation Solutions For catalyst A-1

1. Dissolve 0.160 g $NH_4ReO_4$ and 0.138 g $LiNO_3$ in 3.0 ml of deionized water.

2. Dissolve 0.164 g $HfOCl_2.8H_2O$ (hafnium oxychloride octahydrate) in 2.0 ml saturated aqueous $(NH_4)_2CO_3$ solution.

3. Dissolve 0.058 g CsOH in 0.19 ml $H_2O$.

4. With stirring, add the solutions from step 1, 2 and 3, and 20.3 g of deionized water to 178.7 grams of stock silver solution from Part A to make total weight of 204 grams of impregnation solution.

5. One-fourth of this solution is used for the carrier impregnation to prepare the catalyst A-1. As shown in Table III, Catalyst A-1 using this impregnation solution following the impregnation and curing procedures in Part C below will yield catalysts which contain approximately 13.5% w Ag by weight of the total catalyst, 1.5 micromoles of rhenium, 5.0 micromoles of lithium, 380 ppm of cesium, and 1.0 micromoles of hafnium, expressed as the metal, by weight of the total catalyst. The catalysts are approximately optimum in cesium for the given silver and rhenium levels and support with regard to initial selectivity under the test conditions described below. For Catalysts A-2 and A-3: The procedure for Catalyst A-1 is followed, except that different amounts of Hf and Cs are added to the impregnation solutions which were calculated to result in different levels of Hf and Cs loadings as shown in Table III.

Part C

Catalyst Impregnation and Curing

A catalyst carrier having the properties described below was used in Catalysts A-1, A-2 and A-3:

TABLE II

| Properties of Carrier | |
|---|---|
| Alpha Alumina | ~99% |
| Water absorption | 61.1% |
| Crush strength, lbs | 24.9 |
| % >=12 | 98 |
| % <=9 | 1.0 |
| **Surface Area, sq.m./gm | 0.48 |
| *Total Pore Volume | 0.421 |
| Nitric Acid Leachables in ppm | |
| Na | 50–150 |
| K | 65 Max |
| Ca | 800–1000 |
| Aluminum | 450–600 |
| $SiO_2$ | 1300–1700 |
| Leachables in ppm | |
| Na (Water Test) | 42.9 |
| Na (Acetic Acid Test) | 89.3 |
| K (Water Test) | 23.7 |
| K (Acetic Acid Test) | 52.7 |

*Measured by Micromeritics 9310 Poresizer
**Measured on Micromeritics 2600 Surface Area Analyzer The carrier was impregnated as follows: Approximately 30 grams of the carrier was placed under 25 mm vacuum for 3 minutes at room temperature. Approximately 50 g of the impregnating solution from Part B above was then introduced to submerge the carrier, and the vacuum was maintained at 25 mm for an additional 3 minutes. At the end of this time, the vacuum was released, and the excess impregnating solution was removed from the carrier by centrifugation for 2 minutes at 500 rpm. The impregnated carrier was then cured by being continuously shaken in a 300 cu.ft./hr. air stream at 250° C. for 5 minutes. The cured catalysts were ready for testing.

TABLE III

Compositions of the Catalysts

| Catalyst | Group IVB | Re* | Li* | Cs** | Hf* | Zr* |
|---|---|---|---|---|---|---|
| A-1 | HfOCl$_2$ | 1.5 | 5.0 | 380 | 1.0 | 0.0 |
| A-2 | HfOCl$_2$ | 1.5 | 5.0 | 420 | 0.6 | 0.0 |
| A-3 | HfOCl$_2$ | 1.5 | 5.0 | 420 | 0.3 | 0.0 |
| B-1 | ZrOCl$_2$ | 1.5 | 5.0 | 340 | 0.0 | 0.5 |
| B-2 | ZrOCl$_2$ | 1.5 | 5.0 | 340 | 0.0 | 0.5 |
| B-3 | ZrO(NO$_3$)$_2$ | 1.5 | 5.0 | 380 | 0.0 | 0.5 |
| C-1 | HfSO$_4$ | 1.5 | 8.0 | 540 | 0.55 | 0.0 |
| C-2 | HfSO$_4$ | 1.2 | 8.0 | 540 | 0.55 | 0.0 |
| C-3 | Zr(NO$_3$)$_4$ | 1.5 | 8.0 | 440 | 0.0 | 0.5 |
| C-4 | (NH$_4$)$_2$ZrF$_6$ | 1.5 | 8.0 | 420 | 0.0 | 0.5 |
| Standard | | 1.5 | 5.0 | 350–550 | 0.0 | 0.0 |

*micromoles/gram of catalyst
**parts per million by weight of total catalyst

The actual silver content of the catalyst can be determined by any of a number of standard, published procedures. The actual level of rhenium on the catalysts prepared by the above process can be determined by extraction with 20 mM aqueous sodium hydroxide solution, followed by spectrophotometric determination of the rhenium in the extract. The actual level of hafnium on the catalyst by the above process can be determined by total acid digestion followed by inductively coupled plasma jet analysis (Direct Current Plasma Atomic Emission Technique). The actual level of zirconium on the catalyst by the above process can be determined by total acid digestion followed by inductively coupled plasma jet analysis (Direct Current Plasma Atomic Emission Technique). The actual level of cesium on the catalyst can be determined by employing a stock cesium hydroxide solution, which has been labeled with a radioactive isotope of cesium, in catalyst preparation. The cesium content of the catalyst can then be determined by measuring the radioactivity of the catalyst. Alternatively, the cesium content of the catalyst can be determined by leaching the catalyst with boiling deionized water. In this extraction process cesium, as well as the other alkali metals, it is measured by extraction from the catalyst by boiling 10 grams of whole catalyst in 25 milliliters of water for 5 minutes, repeating the above two more times, combining the above extractions and determining the amount of alkali metal present by comparison to standard solutions of reference alkali metals using atomic absorption spectroscopy (using Varian Techtron Model 1200 or equivalent). It should be noted that the cesium content of the catalyst as determined by the water leaching technique may be lower than the cesium content of the catalyst as determined by the radiotracer technique.

Part D
Standard Microreactor Catalyst Test Conditions/Procedures

The following describes the microreactor catalyst test conditions and procedures used in Illustrative Embodiment 1 to test the catalysts for the production of ethylene oxide from ethylene and oxygen.

Three to five grams of crushed catalyst (14–20 mesh) are loaded into a 0.23 inch internal diameter stainless steel U-shaped tube. The U tube is immersed in a molten metal bath (heat medium) and the ends are connected to a gas flow system. The weight of catalyst used and the inlet gas flow rate are adjusted to achieve a gas hourly space velocity of 3300 cc of gas per cc of catalyst per hour. The inlet gas pressure is 210 psig.

The gas mixture passed through the catalyst bed (in once through operation) during the entire test run (including startup) consists of 30% ethylene, 8.5% oxygen, 5% CO$_2$, 0.5% argon, balance nitrogen, and 0.5 to 5 ppmv ethyl chloride.

Prior to being contacted with the reactant gases, the catalysts are typically pretreated with nitrogen gas at 225° C. for 3 hours.

The initial reactor (heat medium) temperature is 225° C. After 1 hour at this initial temperature, the temperature is increased to 235° C. for 1 hour, followed by 245° C. for 1 hour. The temperature is then adjusted so as to achieve a constant oxygen conversion level of 40% (T$_{40}$). The moderator level is varied and run for 4–24 hours at each moderator level to determine the optimum moderator level for maximum selectivity. Performance data at the optimum moderator level and at T$_{40}$ are usually obtained when the catalyst has been onstream for a total of at least 36 hours and are provided in the illustrative embodiments given below. Due to slight differences in feed gas composition, gas flow rates, and the calibration of analytical instruments used to determine the feed product gas compositions, the measured selectivity and activity of a given catalyst may vary slightly from one test run to the next. To allow meaningful comparison of the performances of catalysts tested at different times, all catalysts described in this illustrative embodiment were tested simultaneously with a standard reference catalyst.

Catalysts B-1, B-2, B-3

Experimental Catalysts Promoted by Zr Oxycation-containing Compounds

Catalysts B-1, B-2 and B-3 were prepared following the same procedures as described above for Catalyst A-1 using a carrier with similar properties as that listed in Table II, except that zirconium oxycation-containing salts, ZrOCl$_2$ or ZrO(NO$_3$)$_2$ were used in lieu of HfOCl$_2$. The approximate levels of dopant loaded are shown in Table II.

Catalysts C-1, C-2, C-3 and C-4

Experimental Catalysts Promoted by Non-Oxycation-containing Hf or Zr Compounds

Catalysts C-1, C-2, C-3 and C-4 were prepared following the same procedures as described above in Illustrative Embodiment I using a carrier with similar properties as that listed in Table II, except that Group IVB metals are provided in non-oxycation-containing forms. HfSO$_4$ was used for Catalysts C-1 and C-2, Zr(NO$_3$)$_4$ was used for Catalyst C-3 and (NH$_4$)$_2$ZrF$_6$ was used for Catalyst C-4. The approximate dopant levels loaded were listed in Table II.

Standard Catalysts without Group IVB Metals

A large number of standard catalysts were prepared in a manner similar to Catalysts A-1,2,3 and B-1,2,3, except that no Group IVB compound is present in the impregnation solutions. The loadings of lithium, rhenium, and silver were the same as Catalysts A-1,2,3 and B-1,2,3. Catalysts with various cesium loadings, from 350 ppm to 550 ppm were prepared to obtain standard catalysts having optimum selectivities at T$_{40}$ matching that of Catalysts A-1,2,3, B-1,2,3 and C-1,2,3. A large database of the performances of these standard catalysts was established. The compositions of the resulted standard catalysts is shown in Table III above.

Results

The catalysts above were tested using the above process, the results thereof are given in Table IV below. Activity data are expressed as the temperature at which the catalyst achieve 40% oxygen conversion of 40% (T$_{40}$). T$_{40}$ of experimental catalysts are compared to corresponding T$_{40}$ of the standard catalysts containing no Group IVB ingredient that performs at the same selectivity.

As shown from the results given in Table IV below, the experimental catalysts prepared from the impregnation solutions containing either hafnium oxycation-containing salts (Catalysts A-1, A-2, and A-3) or zirconium oxycation-containing salts (Catalysts B-1, B-2, B-3) exhibit substantial improvement in initial activities as illustrated by the lower $T_{40}$ required to reach 40% conversion, as compared with the corresponding standard catalysts without group IVB ingredients. However, the experimental catalysts prepared from the impregnation solutions containing group IV metal ingredients in the non-oxycation-containing form (Catalysts C-1, C-2, C-3, and C-4) exhibit no improvement in initial activities.

TABLE IV

| Group IVB Containing Catalyst | Group IVB Compound | Group IVB Catalyst Performance | | Standard Catalyst Activity At Same Selectivity |
|---|---|---|---|---|
| | | $S_{40}$ (%) | $T_{40}$ (°C.) | $T_{40}$ (°C.) |
| A-1 | HfOCl$_2$ | 84.5 | 241 | 254 |
| A-2 | HfOCl$_2$ | 86.0 | 250 | 262 |
| A-3 | HfOCl$_2$ | 85.7 | 247 | 261 |
| B-1 | ZrOCl$_2$ | 85.0 | 248 | 258 |
| B-2 | ZrOCl$_2$ | 84.8 | 249 | 258 |
| B-3 | ZrO(NO$_3$)$_2$ | 84.8 | 242 | 258 |
| C-1 | HfSO$_4$ | 86.1 | 259 | 259 |
| C-2 | HfSO$_4$ | 83.0 | 244 | 244 |
| C-3 | Zr(NO$_3$)$_4$ | 84.4 | 252 | 254 |
| C-4 | (NH$_4$)$_2$ZrF$_6$ | 84.1 | 256 | 253 |

ILLUSTRATIVE EMBODIMENT 2

Catalyst A-4 was prepared in the same manner and on the same carrier as Catalyst A-1 described in Illustrative Embodiment 1. The amounts of rhenium/lithium/hafnium oxychloride loaded on the carrier were 1.5/5.0/1.0 micromoles per gram of carrier. The cesium loading was 387 ppm.

The comparison catalyst SA-4 was prepared in the same manner as catalyst A-4 on the same carrier. Rhenium/lithium loadings were 1.5/5/0 micromoles per gram of carrier. No hafnium salt was loaded. The cesium loading was 480 ppm.

Catalysts A-4 and SA-4 were microreactor tested by the same process as described in Illustrative Embodiment 1 above, except that the test continued for 215 days. The results are shown in Table V below. The Hafnium oxyhalide impregnated catalyst A-4 exhibited an improved initial activity, improved final activity after 215 days, and improved final selectivity after 215 days, relative to the standard catalyst SA-4. (* The end-of-run selectivities (15 day averages) for SA-4 and A-4 (Hf) were 75.8% and 78.2%, respectively).

As mentioned previously, increasing catalytic activity as well as holding activity and selectivity stability to achieve longer catalyst life for rhenium promoted catalysts is of tremendous economic importance. The data suggest that the addition of hafnium oxycation-containing salts to the impregnation solution provides an improvement in both the initial catalytic activity and long-term performance.

TABLE V

| Catalyst | HfOCl$_2$ μm/g | Initial $T_{40}$ °C. | Final $T_{40}$ °C. | Initial $S_{40}$ % | Final $S_{40}$ % |
|---|---|---|---|---|---|
| Catalyst A-4 | 1.0 | 249 | 265 | 85.4 | 78.1 |
| Comparative Catalyst SA-4 | 0 | 260 | 277 | 84.8 | 76.3 |

ILLUSTRATIVE EMBODIMENT 3

Catalyst A-5 was prepared in the same manner as Catalyst A-1 described in Illustrative Embodiment 1, except a carrier having the compositions and the properties listed in TABLE VI and TABLE VII for the preparation of the catalyst. The amounts of rhenium/lithium/hafnium oxychloride loaded on the carrier were 1.5/12.0/0.75 micromoles per gram of carrier. The cesium loading was 540 ppm.

The comparison catalyst SA-5 was prepared in the same manner as catalyst A-5 on the same carrier. Rhenium/lithium loadings were 1.5/12.0 micromoles per gram of carrier. No hafnium salt was loaded. The cesium loading was 580 ppm.

Catalyst A-6 was prepared in the same manner as Catalyst A-5 described above, except 1.5 micromole of sulfate per gram of carrier was loaded. The amounts of rhenium/ lithium/sulfate/hafnium oxychloride loaded on the carrier were 1.5/12.0/1.5/0.75 micromoles per gram of carrier. The cesium loading was 660 ppm.

The comparison catalyst SA-6 was prepared in the same manner as catalyst A-6 on the same carrier. Rhenium/ lithium/sulfate loadings were 1.5/12.0/1.5 micromoles per gram of carrier. No hafnium salt was loaded. The cesium loading was 680 ppm.

TABLE VI

| CARRIER COMPOSITION | |
|---|---|
| Alpha Alumina #1[1,2] | 46.6 |
| Alpha Alumina #2[1,3] | 28.0 |
| Alpha Alumina #3[1,4] | None |
| Alpha Alumina #4[1,5] | None |
| Alpha Alumina #5 (Seed)[1,6] | 0.9 |
| TiO$_2$[1] | 0.2 |
| ZrO$_2$[1] | None |
| Gibbsite[1,7] | 18.7 |
| Boehmite[1,8] | 4.5 |
| Ceramic Bond[1,9,11,12] | 1.3 |
| Organic Burnout[10] | 11.0 |
| Vaseline[10] | 5.0 |
| Boric Acid[10] | 0.15 |
| Water (to make extrudable)[13] | ~30 |

[1]Indicates "ceramic components" and percentages given are based on 100% of the ceramic components.
[2]"Alpha Alumina #1" is an alpha alumina that had a median particle size of about 3 to about 3.4 microns, a BET surface area of about 0.9 to about 1.4 m$^2$/g, a crystallite size of about 1.6 to about 2.2 microns and a soda content of about 0.02% to about 0.06%.
[3]"Alpha Alumina #2" is an alpha alumina with a median particle size of about 4.0 to about 8.0 microns, a surface area of about 3.0 to about 5.0 m$^2$/g, a crystallite size of from about 0.4 to about 0.8 micron and a soda content of about 0.1% to about 0.3%.
[4]"Alpha Alumina #3" is an alpha alumina that had a median particle size of 3.6 to 4.2 microns, a BET surface area of about 0.8 to about 1.0 m$^2$/g, a crystallite size of 3 to 4 microns and a soda content of about 0.05%.
[5]"Alpha Alumina #4" is an alpha alumina that had a median particle size of 2.5 to 3.5 microns, a BET surface area of about 3 to about 4 m$^2$/g, a crystallite size of 3 to 4 microns and a soda content of about 0.1%.

TABLE VI-continued

CARRIER COMPOSITION

[6]"Alpha Alumina #3" is an alpha alumina that was used as the seed for the gibbsite and boehmite precursors of alpha alumina. Its median particle size was less than 0.1 micron.
[7]The gibbsite had a median particle size of from about 4.0 to about 20 microns.
[8]The boehmite was dispersible as a sol.
[9]The ceramic bond for carriers A and B contained components, expressed as the oxides, in the following approximate proportions: 60% wt. silica, 29% wt. alumina, 3% wt. calcium oxide, 2% magnesia, 4% wt. alkali metal oxides and less than 1% wt. each of ferric oxide and titania.
[10]Percentages are based on the total weight of the ceramic components.
[11]The ceramic bond for Carrier C contained components, expressed as oxides, in the following approximate proportions: 67% wt. silica, 30% wt. alumina, about 1% wt. each of ferric oxide and titania, and a trace of alkali metal and alkaline earth oxides.
[12]The ceramic bond used for Carrier D was calcium silicate.
[13]Percentages are based on total weigt of solids.

TABLE VII

CARRIER PROPERTIES

| | |
|---|---|
| Water Absorption, %[1] | 38.3 |
| Packing Density, lbs/ft$^3$ [2] | 50.9 |
| Crush Strength, lbs[3] | 14.9 |
| Surface Area, m$^2$/g[4] | 1.01 |
| Acid Leachables, ppm | |
| Na | 350 |
| K | 76 |
| Ca | 149 |
| Al | 579 |
| TiO$_2$, % | 0.2 |
| Firing Temperature, °C. | 1450 |

[1]"Water Absorption" is a measure of the increase in weight of the carrier after being immersed in water and weighed.
[2]"Packing Density" is the settled packing density as measured by ASTM D-4699-87, modified by the use of cylinder with an inside diameter of 3¾ inches and a length of 18 inches, or an equivalent.
[3]"Crush Strength" is measured on a Compton Tensile Tester, model 50-OP.
[4]"Surface Area" is the BET surface area measured using nitrogen or krypton as the adsorbate.

Catalysts A-5 and SA-5 were microreactor tested by the following process:

Three to five grams of crushed catalyst (14–20 mesh) were loaded into a 0.23 inch internal diameter stainless steel U-shaped tube. The U tube was immersed in a molten metal bath (heat medium) and the ends were connected to a gas flow system. The weight of catalyst used and the inlet gas flow rate were adjusted to achieve a gas hourly space velocity of 6800 cc of gas per cc of catalyst per hour. The inlet gas pressure was 210 psig. The gas mixture passed through the catalyst bed (in once-through operation) during the entire test run (including startup) consists of 25% ethylene, 7.0% oxygen, 5% CO$_2$, 0.5% argon, balance nitrogen, and 0.5 to 5 ppmv ethyl chloride. Prior to being contacted with the reactant gases, the catalysts were pre-treated with nitrogen gas at 225° C. for 3 hours.

The initial reactor (heat medium) temperature was 225° C. After 1 hour at this initial temperature, the temperature was increased to 235° C. for 1 hour, followed by 245° C. for 1 hour. The temperature was then adjusted so as to achieve a constant ethylene oxide production level of 1.5% (T$_{3.5}$). The moderator level was varied and run for 4–24 hours at each moderator level to determine the optimum moderator level for maximum selectivity. Performance data at the optimum moderator level and at T$_{1.5}$ were obtained when the catalyst had been onstream for a total of at least 36 hours and are provided in TABLE VIII given below.

TABLE VIII

| Catalyst | Re/SO$_4$/Li µm/g | HfOCl$_2$ µm/g | S$_{1.5}$ % | T$_{1.5}$ °C. |
|---|---|---|---|---|
| Catalyst A-5 | 1.5/0/12 | 0.75 | 86.3 | 242 |
| Comparative Catalyst SA-5 | 1.5/0/12 | 0 | 85.0 | 246 |
| Catalyst A-6 | 1.5/1.5/12 | 0.75 | 86.1 | 242 |
| Comparative Catalyst SA-6 | 1.5/1.5/12 | 0 | 88.9 | 258 |

The ranges and limitations provided in the instant specification and claims are those which are believed to particularly point out a distinctly claim the instant invention. It is, however, understood that other ranges and limitations that perform substantially the same function in substantially the same manner to obtain the same or substantially the same result are intended to be within the scope of the instant invention as defined by the instant specification and claims.

We claim:

1. A process for the production of ethylene oxide comprising the steps of contacting ethylene in the vapor phase with an oxygen-containing gas at ethylene oxide forming conditions at a temperature ranging between about 180° C. and 330° C. in the presence of a catalyst comprising a porous refractory support having deposited thereon a catalytically effective amount of silver, a promoting amount of alkali metal, a promoting amount of rhenium, and a promoting amount of Group IVB metal applied to the support in the form of oxycation-containing compound(s), wherein said Group IVB metal is selected from the group consisting of titanium, zirconium, and hafnium.

2. The process according to claim 1, wherein said Group IB metal is hafnium.

3. The process according to claim 1, wherein the support in said catalyst comprises at least about 85 percent by weight of alpha alumina, having a water pore volume from about 0.1 cc/g to about 0.75 cc/g, and having a surface area from about 0.03 m$^2$/g to about 10 m$^2$/g.

4. The process according to claim 3, wherein the amount of silver is in the range of from about 1 to about 30 percent by weight expressed as the metal based on the total weight of the catalyst, the amount of Group IVB metal is in the range of from about 0.01 micromoles to about 10 micromoles per gram of the total catalyst, expressed as the metal, the amount of alkali metal is in the range of from about 10 to about 3000 parts per million, expressed as the metal, by weight of total catalyst, the amount of rhenium is in the range of from about 0.1 to about 10 micromoles, expressed as the metal, per gram of the total catalyst.

5. The process according to claim 3, wherein said support has a crush strength of at least about 5 pounds and a settled packing density of at least about 30 pounds/cubic foot and which support comprises first and second alpha alumina components with a first alpha alumina component in the form of particles having a median crystallite size of from about 0.4 to about 4 microns providing from about 95% to about 40% of the total weight of alpha alumina in the carrier and a second alpha alumina component generated in situ by a sol-gel process and providing the balance of the alpha alumina in the carrier.

6. The process of claim 2, wherein said hafnium metal applied to the catalyst support is selected from the group consisting of hafnium oxyhalide, hafnium oxynitrate or hafnium oxycarbonate.

7. The process of claim 3, wherein said alkali metal promoter is selected from the group consisting of lithium, potassium, rubidium, cesium, and mixtures thereof.

8. The process of claim 3, wherein said alkali metal promoter comprises cesium.

9. The process of claim 3, wherein said alkali metal promoter comprises cesium plus at least one additional alkali metal.

10. The process of claim 4, wherein said catalyst further comprises a rhenium co-promoter selected from sulfur, molybdenum, tungsten, chromium and mixtures thereof.

11. A process for the epoxidation of olefins having no allylic hydrogen comprising the steps of contacting the olefins in the vapor phase with an oxygen-containing gas maintain at a ratio of olefin to oxygen in the range of 0.01 up to 20, at epoxide forming conditions at a temperature in the range of from about 75° C. to about 325° C. in the presence of an organic halide, inorganic halides, acid halides, or elemental halogens, and a catalyst comprising a porous refractory support having deposited by impregnation thereon a catalytically effective amount of silver, a promoting amount of alkali metal, a promoting amount of rhenium, and a promoting amount of Group IVB metal applied to the support in the form of oxycation-containing compound(s); wherein after the impregnation of the metals, the catalyst is put in intimate contact with a gas comprising a gas containing at least about 4 volume percent of hydrogen.

12. The process according to claim 11, wherein said Group IB metal is hafnium.

13. A process for the production of ethylene oxide comprising the steps of contacting ethylene in the vapor phase with an oxygen-containing gas at ethylene oxide forming conditions at a temperature ranging between about 180° C. and 330° C. in the presence of a catalyst prepared by a process which comprises the steps of:
 (1) impregnating a porous, refractory support with
  (a) a solubilized catalytically effective amount of silver,
  (b) a solubilized promoting amount of alkali metal,
  (c) a solubilized promoting amount of rhenium, and
  (d) a solubilized promoting amount of Group IVB metal in the form of Group IVB metal oxycation-containing compound(s);
 (2) reducing the silver to metallic silver.

14. The process of claim 13, wherein the support is impregnated with sufficient amount of silver, alkali metal, rhenium and hafnium oxycation-containing compounds to deposit on the support
 (i) from about 1 to about 30 percent by weight of silver compound(s) expressed as the metal based on the total weight of the catalyst,
 (ii) from about 0.01 micromoles to about 10 micromoles per gram of the total catalyst of hafnium metal, expressed as the metal, which is applied to the catalyst support in the form of an oxycation-containing compound,
 (iii) from about 10 to about 3000 parts per million of alkali metal, expressed as the metal, by weight of total catalyst,
 (iv) from about 0.1 to about 10 micromoles of rhenium, expressed as the metal, per gram of the total catalyst, to provide the catalyst with a catalytically effective amount of silver, a promoting amount of alkali metal, a promoting amount of rhenium, and a promoting amount of hafnium metal;
wherein said support comprises at least about 85 percent by weight of alpha alumina having a surface area ranging from about 0.03 to about 10 m²/g and has a crush strength of at least about 5 pounds and a settled packing density of at least about 30 pounds/cubic foot and has a pore volume of from about 0.3 to about 0.6 cc/gram; wherein said support comprises first and second alpha alumina components with a first alpha alumina component in the form of particles having a median crystallite size of from about 0.4 to about 4 microns providing from about 95% to about 40% of the total weight of alpha alumina in the carrier and a second alpha alumina component generated in situ by a sol-gel process and providing the balance of the alpha alumina in the carrier; wherein said support comprises from about 0.05% by weight to about 1% by weight of titania, based on the weight of alumina in the carrier.

15. The process of claim 13, wherein in step (1), the impregnated support is heated to between about 50° C. and about 600° C. in the presence of a gas stream selected from the group consisting of (1) air, (2) oxygen containing gas, (3) hydrogen containing gas, (4) an inert gas, and (5) mixtures thereof for a period of time sufficient to reduce a major amount of the silvex to silver metal.

* * * * *